US009066756B2

(12) United States Patent
Wong

(10) Patent No.: US 9,066,756 B2
(45) Date of Patent: Jun. 30, 2015

(54) ORTHOPEDIC EXTERNAL FIXATION DEVICE

(71) Applicant: Kian-Ming (Kevin) Wong, Lakeland, TN (US)

(72) Inventor: Kian-Ming (Kevin) Wong, Lakeland, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 72 days.

(21) Appl. No.: 13/896,060

(22) Filed: May 16, 2013

(65) Prior Publication Data

US 2014/0046326 A1 Feb. 13, 2014

Related U.S. Application Data

(63) Continuation of application No. 13/568,302, filed on Aug. 7, 2012, now Pat. No. 8,454,604, which is a continuation of application No. 12/711,591, filed on Feb. 24, 2010, now Pat. No. 8,257,353.

(51) Int. Cl.
*A61B 17/62* (2006.01)
*A61B 17/64* (2006.01)

(52) U.S. Cl.
CPC .............. *A61B 17/62* (2013.01); *A61B 17/6416* (2013.01)

(58) Field of Classification Search
CPC ........................... A61B 17/6416; A61B 17/62
USPC ........................ 606/54–60, 96, 329, 250–268, 606/270–278, 324; 403/373, 374.3, 398, 403/400; 411/544; 24/486, 569, 135 R, 24/135 N
See application file for complete search history.

(56) References Cited

U.S. PATENT DOCUMENTS

| | | | |
|---|---|---|---|
| 3,941,123 A | 3/1976 | Volkov et al. | |
| 3,985,127 A | 10/1976 | Volkov et al. | |
| 3,993,055 A | 11/1976 | Volkov et al. | |
| 4,100,919 A | 7/1978 | Oganesyan et al. | |
| 4,185,623 A | 1/1980 | Volkov et al. | |
| 4,308,863 A | 1/1982 | Fischer | |
| 4,312,336 A | 1/1982 | Danieletto et al. | |
| 4,768,524 A | 9/1988 | Hardy | |
| 4,890,631 A | 1/1990 | Hardy | |
| 5,728,095 A | 3/1998 | Taylor et al. | |
| 5,752,957 A * | 5/1998 | Ralph et al. | 606/266 |
| 5,797,908 A * | 8/1998 | Meyers et al. | 606/54 |
| 5,863,292 A | 1/1999 | Tosic | |
| 5,928,230 A | 7/1999 | Tosic | |
| 6,030,386 A * | 2/2000 | Taylor et al. | 606/56 |
| 6,129,727 A | 10/2000 | Austin et al. | |
| 6,443,953 B1 * | 9/2002 | Perra et al. | 606/270 |
| 6,500,177 B1 | 12/2002 | Martinelli et al. | |
| 7,261,713 B2 | 8/2007 | Langmaid et al. | |
| 7,282,052 B2 | 10/2007 | Mullaney | |

(Continued)

OTHER PUBLICATIONS

European Search Report issued in corresponding European patent application No. 14173211, dated Sep. 4, 2014, 5 pages.

*Primary Examiner* — Pedro Philogene
(74) *Attorney, Agent, or Firm* — Duane Morris LLP

(57) ABSTRACT

A telescopically adjustable strut for use with orthopedic external fixators has a first end and a second end and includes a universal-hinged connector provided at each of the first and second ends for connecting the strut to orthopedic external fixator base members. The universal-hinged connector is configured and adapted for pivoting the strut relative to the base members and to lock the universal-hinged connector at a desired angle.

17 Claims, 12 Drawing Sheets

(56) References Cited

U.S. PATENT DOCUMENTS

| | | |
|---|---|---|
| 7,306,601 B2 | 12/2007 | McGrath et al. |
| 7,422,593 B2 | 9/2008 | Cresina et al. |
| 8,257,353 B2 | 9/2012 | Wong |
| 8,454,604 B2 | 6/2013 | Wong |
| 2003/0069580 A1 | 4/2003 | Langmaid et al. |
| 2005/0119656 A1* | 6/2005 | Ferrante et al. ............ 606/59 |
| 2009/0036892 A1 | 2/2009 | Karidis et al. |
| 2009/0118733 A1 | 5/2009 | Orsak |
| 2009/0177198 A1 | 7/2009 | Theodoros et al. |

\* cited by examiner

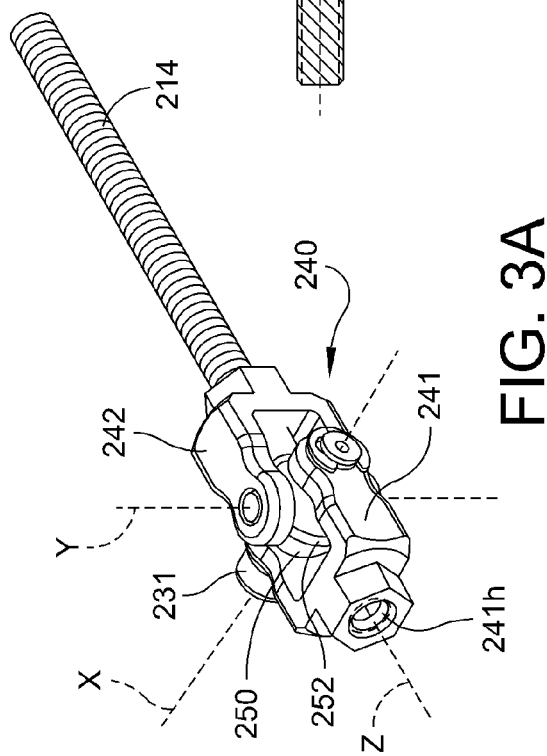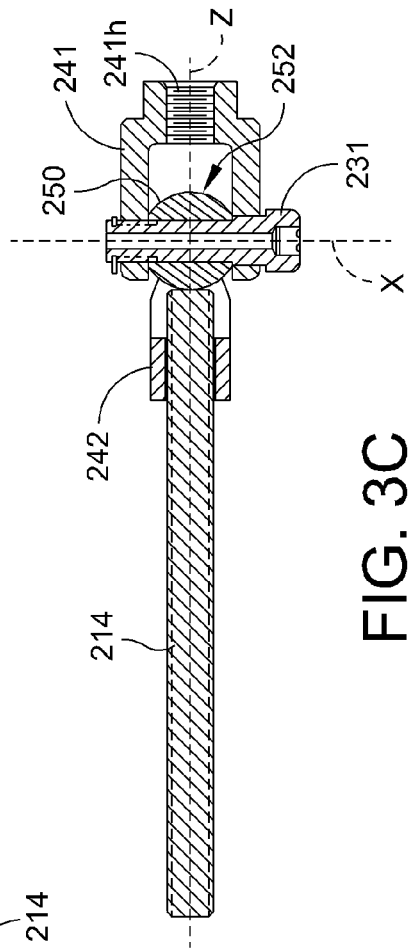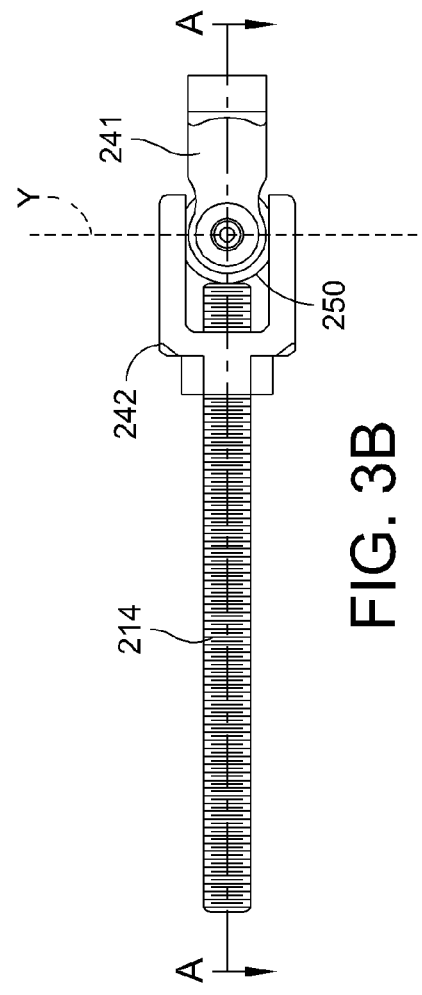

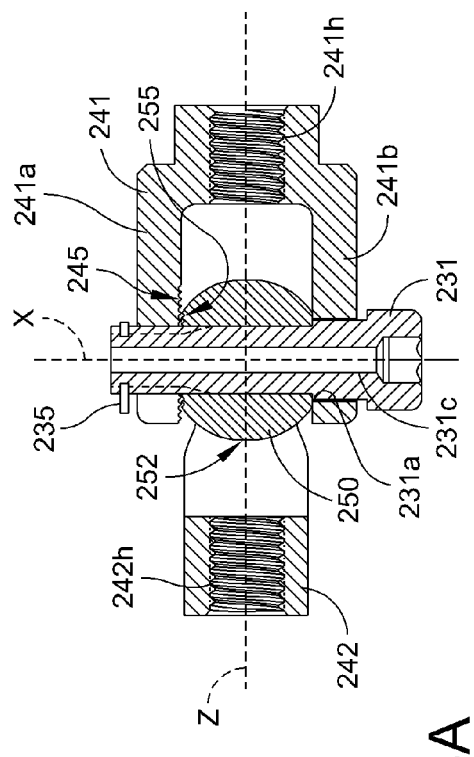
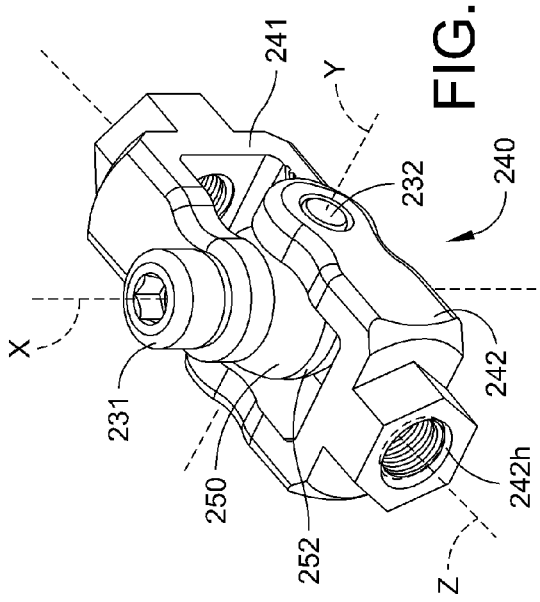
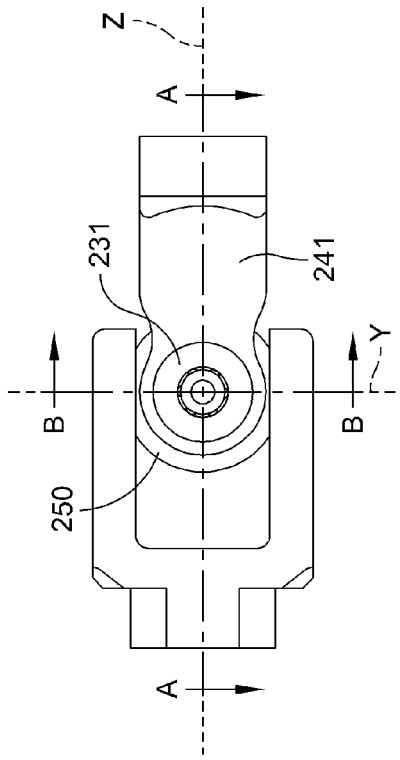
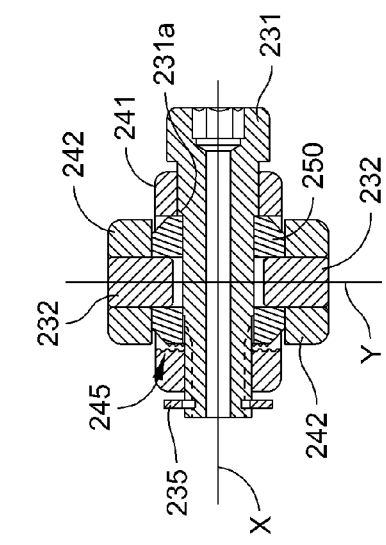

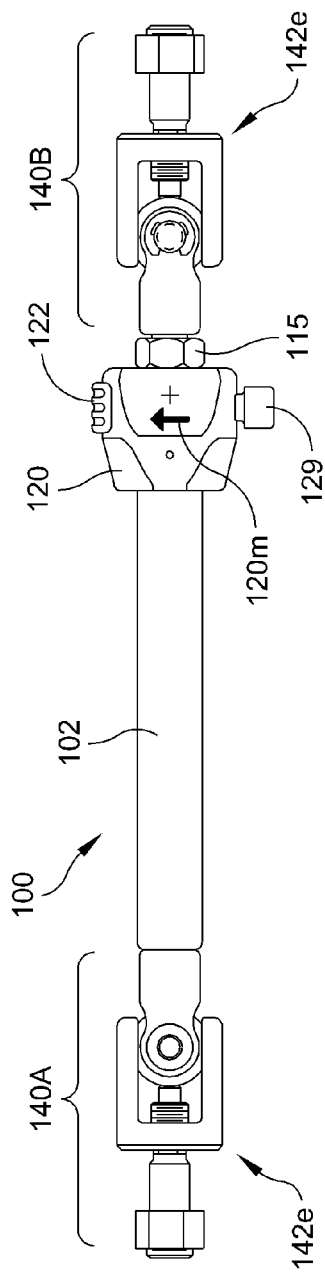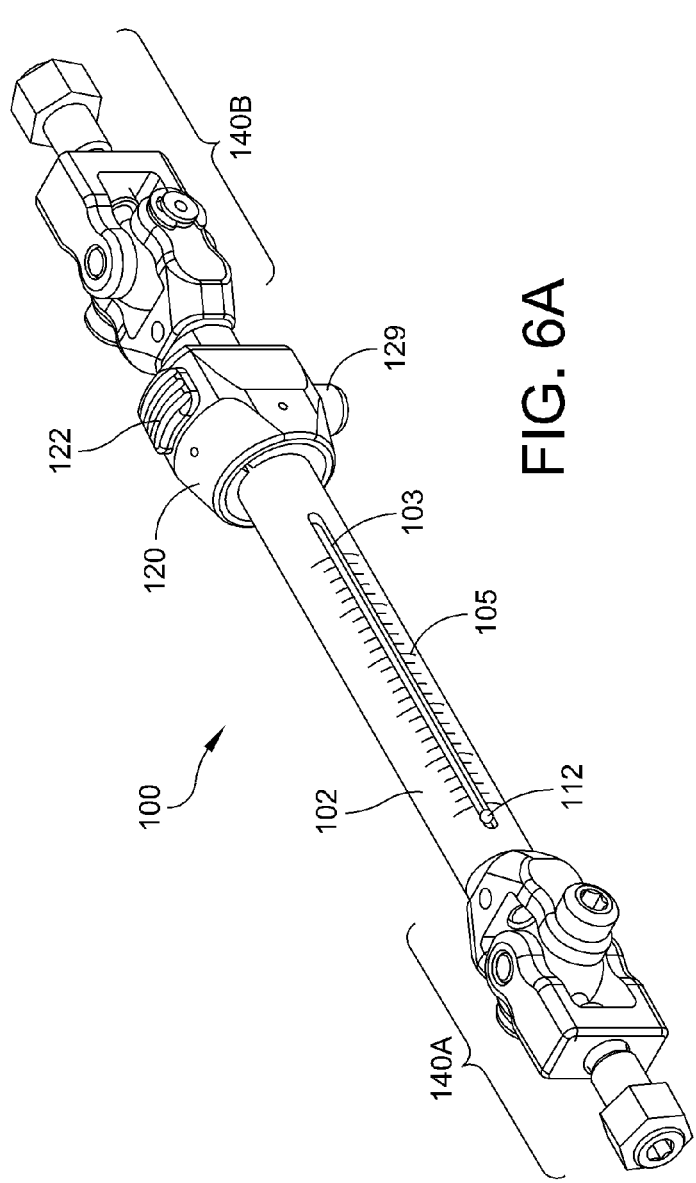
FIG. 5
FIG. 6A

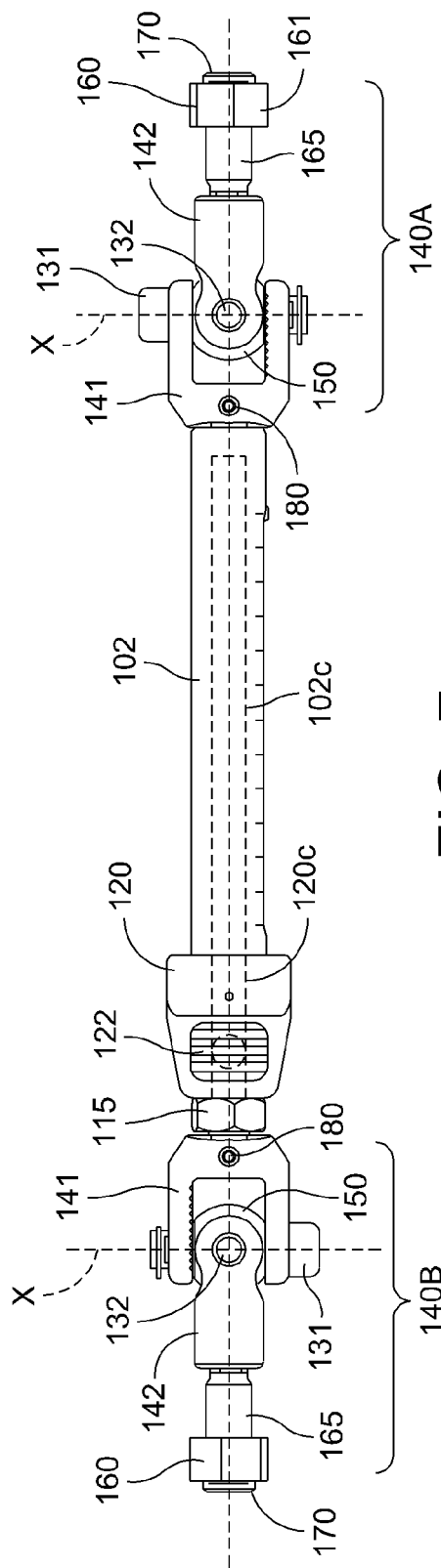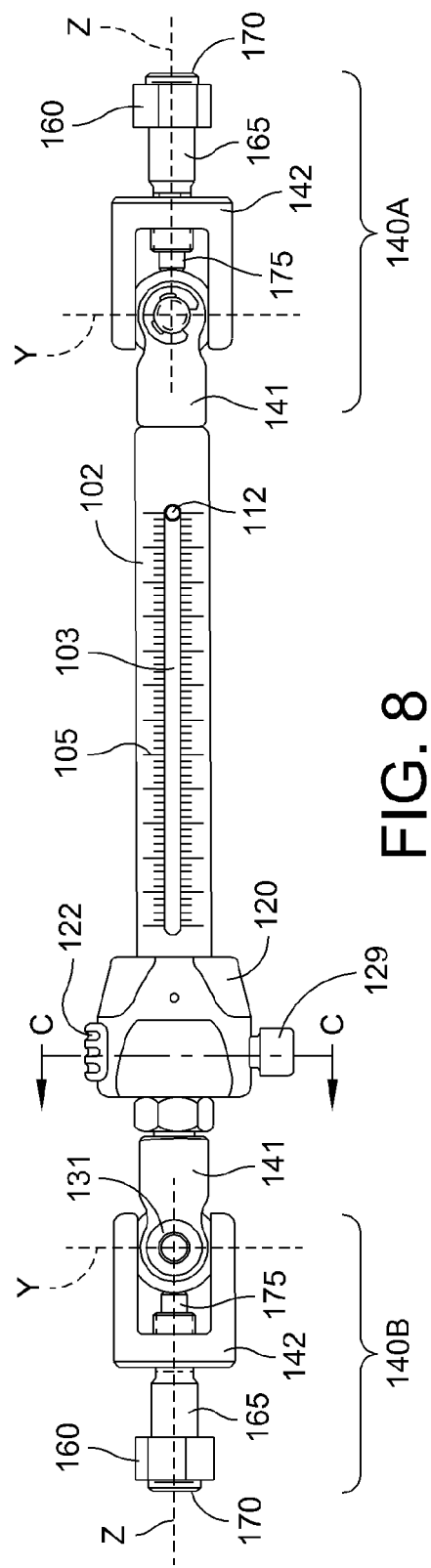
FIG. 7
FIG. 8

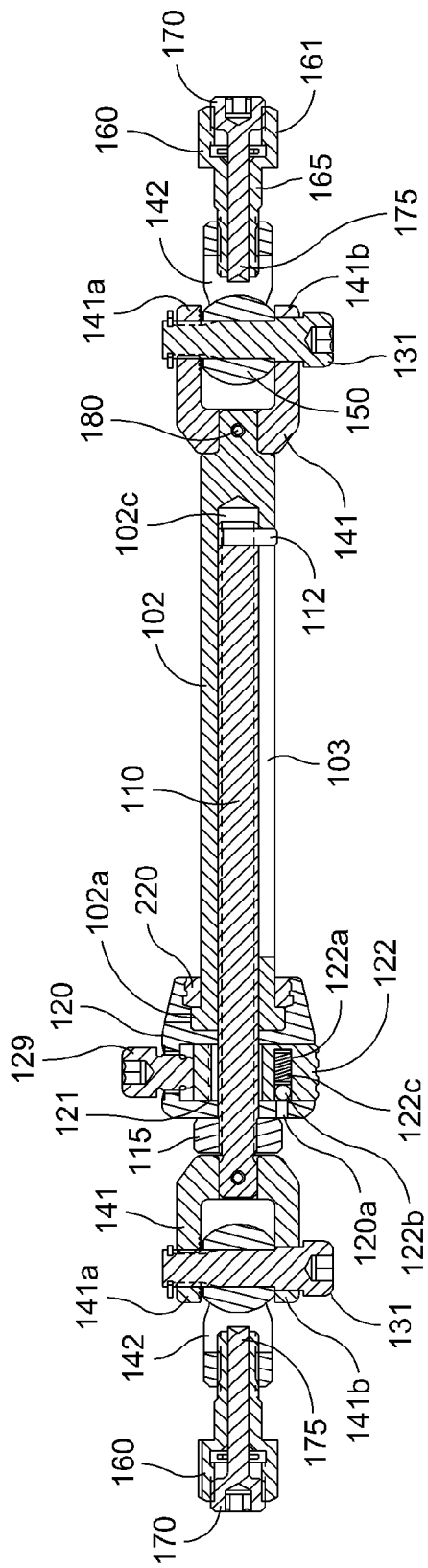
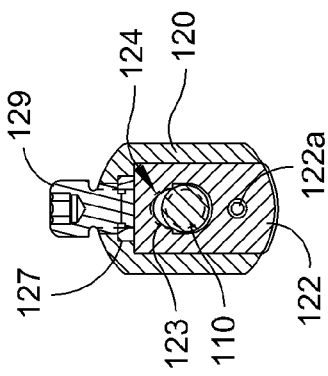
FIG. 9A
FIG. 9B

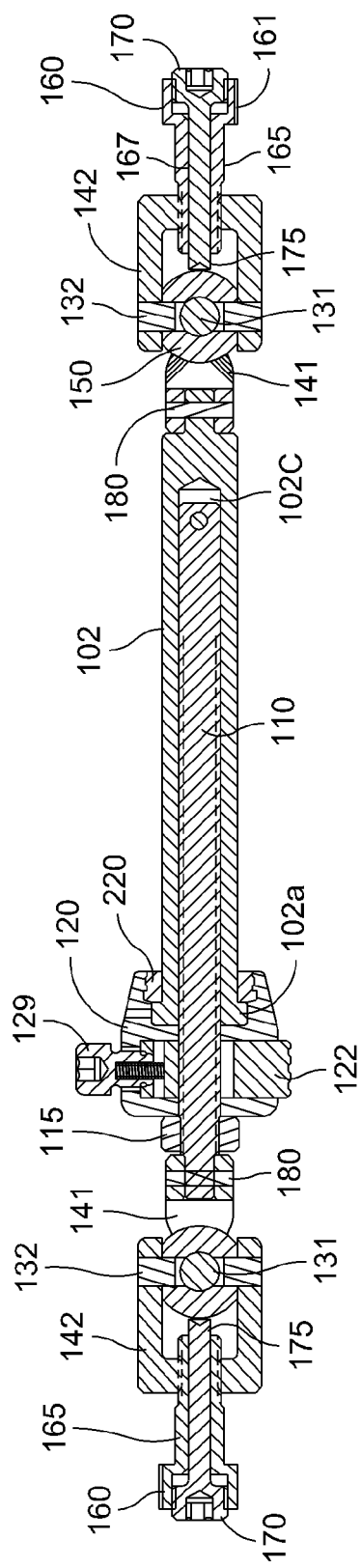
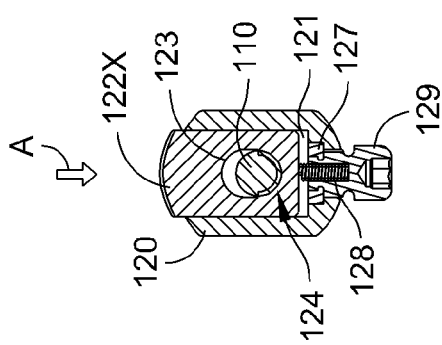
FIG. 10A
FIG. 10B

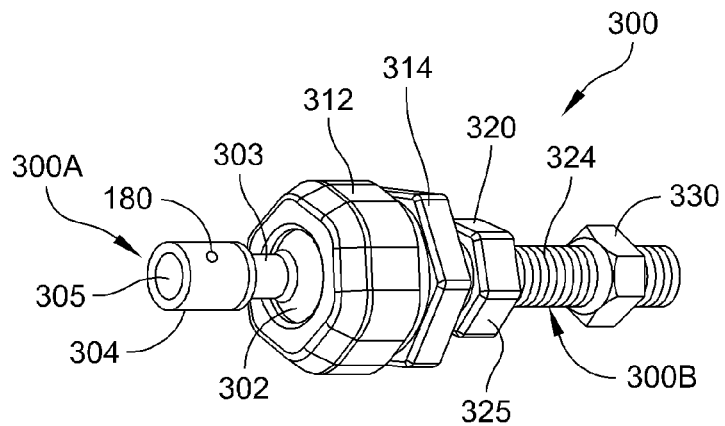
FIG. 11A
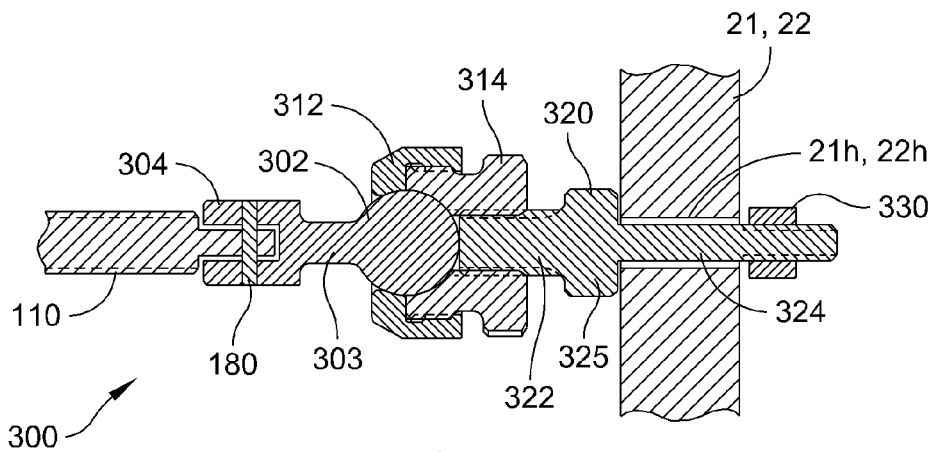
FIG. 11B
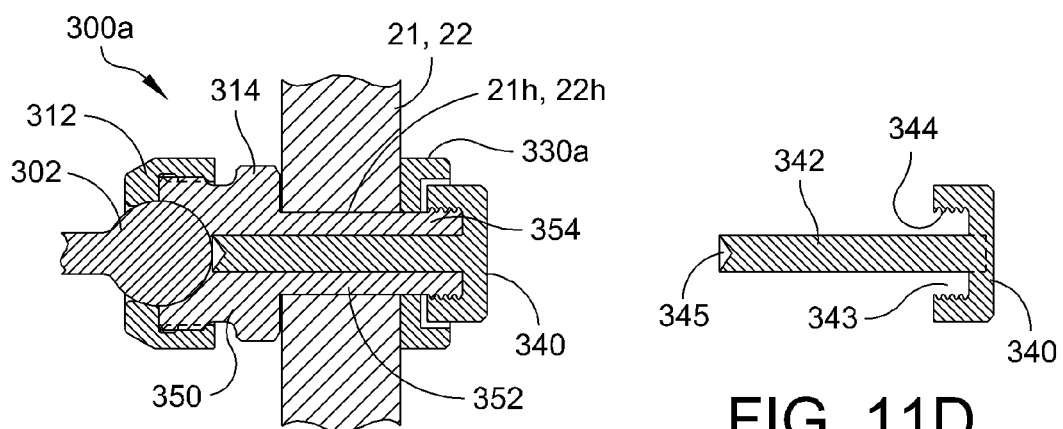
FIG. 11C
FIG. 11D

ORTHOPEDIC EXTERNAL FIXATION DEVICE

CROSS-REFERENCE TO RELATED APPLICATION

This application is a continuation of U.S. patent application Ser. No. 13/568,302, now U.S. Pat. No. 8,454,604, which was filed Aug. 7, 2012 as a continuation of U.S. patent application Ser. No. 12/711,591, which was filed Feb. 24, 2010 and is now U.S. Pat. No. 8,257,353, the entireties of which are herein incorporated by reference.

FIELD OF THE INVENTION

The present disclosure relates to the field of orthopedic devices and more particularly to an external fixation device for providing fixation or immobilization of fractured bone is facilitated by means external to the body soft tissue.

BACKGROUND

Orthopedic external fixation devices are used in many orthopedic treatments to fixate, distract, compress, or reduce bone segments and to correct deformities. Generally, fixation devices or fixators are used to stabilize fractured bone pieces and to facilitate the healing of bones at a bone repair site. Such fixators can be used by orthopedic surgeons to restore the patient's anatomy at a fracture following an injury or distract an osteotomy site in bone lengthening or shortening procedures. One type of external fixation devices comprise two base members connected by one or more of adjustable struts that can be adjusted to set the two base members into a desired relative configuration that is appropriate for treating a particular orthopedic fracture, nonunion, malunion, or deformities of skeletal bone fragments. The base members usually have ring-like structures and can be full rings or partial rings. In one conventional example disclosed in U.S. Pat. No. 6,030,386 to Taylor et al., adjustable telescoping struts connect two ring-like structures via conventional universal-joints that provide a variety of attachment angles. However, the conventional universal-joints do not provide the ability to lock the attachment angle while configuring the external fixation device.

Therefore, there is a continuing need for an improved external fixator and adjustable struts that is simpler to use while maintaining the robust adjustability to be able to configure the external fixators for a variety of orthopedic fixation applications.

SUMMARY

According to an embodiment of the present disclosure, a locking universal joint hinge is disclosed. The locking universal joint hinge has a first and a second orthogonally oriented pivot axes and the universal joint hinge comprises a first-axis clevis connector having a first arm and a second arm and a second-axis clevis connector having a first arm and a second arm. A cross-shaft member is positioned between the two arms of each clevis connectors. A first-axis clevis pin pivotally connects the two arms of the first-axis clevis connector to the cross-shaft member and defines the first pivot axis. A second-axis clevis pin pivotally connects the two arms of the second-axis clevis connector to the cross-shaft member and defines the second pivot axis. The first-axis clevis pin extends from the first arm to the second arm of the first-axis clevis connector and through the cross-shaft member, wherein the first-axis clevis pin is configured and adapted to lock the first pivot axis by urging the cross-shaft member against one of the two arms of the first-axis clevis connector, thereby, causing a surface of the cross-shaft member to contact a surface of the one of the two arms of the first-axis clevis connector and generate a frictional or mechanical interference between the two contacting surfaces.

According to an embodiment of the present disclosure, a telescopically adjustable strut for use with orthopedic external fixators has a first end and a second end and includes a universal joint connector provided at each of the first and second ends for connecting the strut to orthopedic external fixator base members. The universal joint connector is configured and adapted for pivoting the strut relative to the base members and to lock the universal joint connector at a desired angle.

The strut comprises an elongated shaft with a hollow axial center; a lead screw having external threads, one end of the lead screw extending into the axial center of the shaft; and an adjustment knob rotatably attached to one end of the elongated shaft and provided with an axially-oriented opening through which the lead screw extends. A second end of the elongated shaft opposite the adjustment knob defines the first end of the strut and a second end of the lead screw opposite the end extending into the adjustment knob defines the second end of the strut.

The adjustment knob is provided with a release button that is movable between an engaged position and a released position. The release button is configured to threadably engage the external threads of the lead screw when in the engaged position and disengage from the external threads of the lead screw when in the released position. The adjustment knob and the release button are provided with a ball detent arrangement for holding the release button in the released position as the default position. The lead screw and the shaft are configured to prevent axial rotation of the lead screw relative to the shaft, whereby rotation of the adjustment knob when the release button is in the engaged position causes the lead screw to linearly translate along the longitudinal axis of the shaft.

In another embodiment, the release button is configured to be held in the engaged position as the default position. The release button can be spring-biased to hold the release button in the engaged position until moved into the released position.

According to another embodiment of the present disclosure, an orthopedic external fixator is disclosed. The orthopedic external fixator includes a pair of ring-like base members that are connected by a plurality of the telescopically adjustable struts. The pair of ring-like base members can be connected by one or more of the telescopically adjustable struts in combination with one or more of other types of adjustable struts or adjustable hinges.

The ability to quickly release the lead screw button when adjusting the lengths of the adjustable strut makes adjusting the external fixator utilizing the adjustable strut of the present disclosure substantially more efficient than those external fixation systems utilizing conventional struts.

According to another embodiment, additional base members can be added to the orthopedic external fixator beyond the first pair mentioned above and connected to the assembly formed by the first pair by additional plurality of the telescopically adjustable struts.

BRIEF DESCRIPTION OF THE DRAWINGS

FIG. 3A is an isometric view of one of the single-hinged struts shown in FIG. 2 with one of the threaded rods removed from the locking universal joint hinge.

FIG. 3B is a plan view of the single-hinged strut of FIG. 3A.

FIG. 3C is a longitudinal section view of the single-hinged strut of FIG. 3B the section being taken through the line A-A in FIG. 3B.

FIG. 4A is an isometric view of a universal joint shown in FIG. 3A from a different angle.

FIG. 4B is a plan view of the universal joint of FIG. 4A looking down into the X-axis.

FIG. 4C is a cross-sectional view of the universal joint of FIG. 4A wherein the section is taken through the plane A-A in FIG. 4B.

FIG. 4D is a cross-sectional view of the universal joint of FIG. 4A wherein the section is taken through the plan B-B shown in FIG. 4B.

FIG. 5 is a plan view of a preferred embodiment of the adjustable strut of the external fixator of FIGS. 1 and 2 in its retracted configuration.

FIG. 6A is an isometric view of the adjustable strut of FIG. 5 in its retracted configuration.

FIGS. 7 and 8 are additional plan views of the adjustable strut of FIG. 5.

FIG. 9A is a longitudinal cross-sectional view of one embodiment of the adjustable strut of the present disclosure with the adjustment knob in the released position.

FIG. 9B is a transverse cross-sectional view through the adjustment knob shown in FIG. 9A in the released position.

FIG. 10A is a longitudinal cross-sectional view of another embodiment of the adjustable strut of the present disclosure with the adjustment knob in the engaged position.

FIG. 10B is a transverse cross-sectional view through the adjustment knob shown in FIG. 10A in the engaged position.

FIG. 11A is an isometric view of a ball-joint embodiment of the universal-hinged connector of the adjustable strut of the present disclosure.

FIG. 11B is a longitudinal cross-sectional view of the ball-joint embodiment of FIG. 11A.

FIGS. 11C and 11D illustrate another example of a ball-joint in accordance with some embodiments.

The features shown in the above referenced drawings are illustrated schematically and are not intended to be drawn to scale nor are they intended to be shown in precise positional relationship. Like reference numbers indicate like elements.

DETAILED DESCRIPTION

In the following detailed description of the preferred embodiments, reference is made to the accompanying drawings which form a part hereof, and in which are shown by way of illustration specific embodiments in which the invention may be practiced. Other embodiments may be utilized and structural changes may be made without departing from the scope of the present invention.

Figure 1:
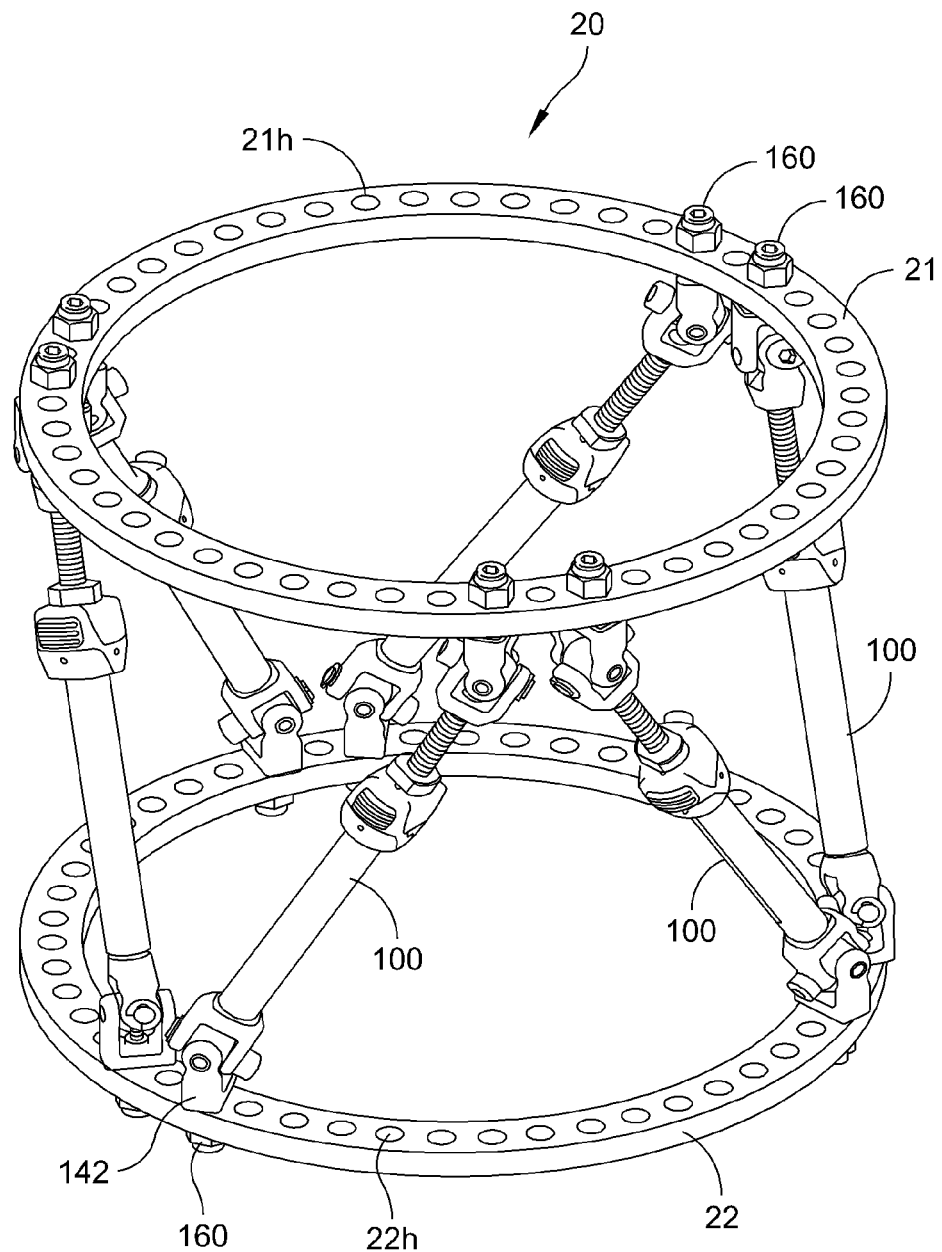
FIG. 1 is perspective view of a preferred embodiment of an orthopedic external fixator of the present disclosure.

Referring to FIG. 1, an orthopedic external fixator 20 according to a preferred embodiment will be described. The orthopedic external fixator 20 generally includes a pair of base members 21, 22 that have ring-like structures that are connected by a plurality of telescopically adjustable struts 100. Each of the ring-like base members 21, 22 can be a fully encircling ring as shown or a partial ring, such as a generally U-shaped foot ring.

In the illustrated example, the two base members 21, 22 are connected by six telescopically adjustable struts 100. The telescopically adjustable struts 100 enable the orthopedic surgeon to configure and adjust the orientation of the two base members 21, 22 relative to each other by adjusting the lengths of each strut 100. Such feature of the external fixator 20 is useful for treating a variety of fractures, nonunions, deformities and malunions of skeletal bone fragments.

Figure 2:
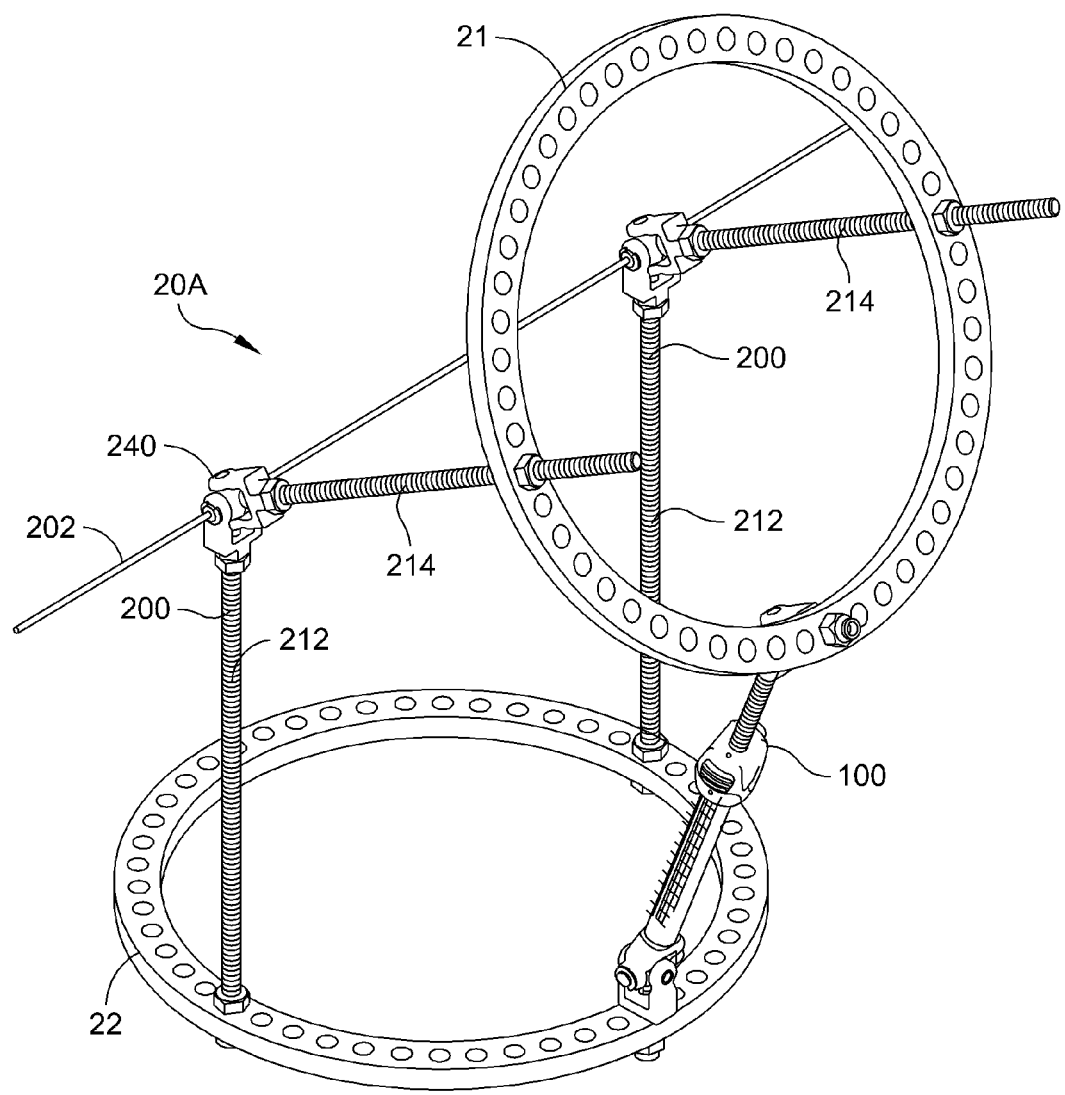
FIG. 2 is a perspective view of another embodiment of an orthopedic external fixator of the present disclosure.

The actual number of telescopically adjustable struts 100 used in combination with the base members 21, 22 can be different depending upon the needs of the particular application. This is especially true where different types of adjustable struts or hinges are utilized in conjunction with the adjustable struts 100 in configuring the external fixator 20. FIG. 2 illustrates an example of such orthopedic external fixator 20A, in which two ring-like base members 21, 22 are connected by one telescopically adjustable strut 100 and two single-hinged struts 200.

The single-hinged struts 200 include two threaded rods 212, 214 joined by a locking universal joint hinge 240. The axes of the locking universal joint hinges 240 are configured to lock the universal joint hinges 240 at a desired angle. The two threaded threaded rods 212, 214 connect to the universal joint hinge 240 by threading into the universal joint hinge 240 from opposite ends. As shown in FIG. 2, the universal joint hinges 240 can be configured to receive a wire 202 therethrough so that in the assembled arrangement 20A, the wire 202 can be extended through the universal joint hinges 240 of two oppositely positioned single-hinged struts 200 for aligning the single-hinged struts 200.

Referring to FIGS. 3A-3C and 4A-4D, the structure of the locking universal joint hinge 240 will be described in more detail. FIG. 3A shows the locking universal joint hinge 240 with one of the two threaded rods 212 threaded into the universal joint hinge 240 while the other threaded rod 214 has been removed for illustration purposes.

The isometric views of the universal joint hinge 240 in FIGS. 3A and 4A show two pivot axes X and Y associated with the universal joint hinge 240. The locking universal joint hinge 240 comprises two clevis connectors, an X-axis clevis 241 and a Y-axis clevis 242 that are pivotally connected by a cross-shaft member 250. An X-axis clevis pin 231 pivotally connects the X-axis clevis 241 to the cross shaft member 250 and allows the X-axis clevis 241 to pivot about the first pivot axis X. A Y-axis clevis pin 232 pivotally connects the Y-axis clevis 242 to the cross shaft member 250 and allows the Y-axis clevis 242 to pivot about the second pivot axis Y. It should be noted that in the illustrated embodiment, the cross-shaft member 250 is configured to have the X and Y pivot axes intersect orthogonally. Therefore, while the X-axis clevis pin 231 is a single piece pin extending through the cross-shaft member 250 as shown in the cross-sectional views of FIGS. 3C and 4C, the Y-axis clevis pin 232 comprises two pieces pivotally connecting the Y-axis clevis 242 to the cross-shaft member 250 as shown in FIG. 4D. To allow for the wire 202 described above, the X-axis clevis pin 231 is provided with a cannula 231c extending longitudinally therethrough as shown in FIGS. 3C and 4C.

Each of the X-axis clevis 241 and the Y-axis clevis 242 are provided with threaded holes 241h, 242h, respectively, for receiving the threaded rods 212, 214. The threaded holes 241h, 242h are oriented so that their threading axes are orthogonal to their respective X and Y pivot axes. In other words, the longitudinal axis of the threaded hole 241h is orthogonal to the pivot axis X and the longitudinal axis of the threaded hole 242h is orthogonal to the pivot axis Y. Thus, when the two clevis connectors 241, 242 are positioned as shown in FIGS. 3A and 4A with the threaded holes 241h, 242h at opposite ends of the universal joint hinge 240, the threaded rods 212, 214 threaded into the internally threaded holes 241h, 242h will be axially aligned along the axis Z.

Referring to FIGS. 3C and 4C, the X-axis clevis pin 231 is structured like a bolt and has a head and a shaft. The head of the X-axis clevis pin 231 will be referred to herein as the proximal end of the pin and the opposite end of the shaft will be referred to as the distal end of the pin. The X-axis clevis 241 has a generally U-shaped structure and has two arms 241a, 241b with the cross-shaft member 250 positioned in between the two arms. The shaft of the X-axis clevis pin 231 extends from the first arm 241a, through the cross shaft member 250, to the second arm 241b through holes provided in the arms 241a, 241b. The distal end of the X-axis clevis pin 231 threadably engages the arm 241a and is held in place. In order to prevent unintentional removal of the X-axis clevis pin 231, the distal end of the pin can be mechanically secured. In the example shown, a snap ring 235 is used to keep the X-axis clevis pin 231 from being removed. In another example, a cotter pin or other suitable mechanical means can be used in place of the snap ring 235.

According to a preferred embodiment, the universal joint hinge 240 is configured for locking the X and Y pivoting axes of the X-axis clevis 241 and the Y-axis clevis 242. The X axis can be locked by tightening the X-axis clevis pin 231. The shaft of the X-axis clevis pin 231 has a larger diameter than the rest of the shaft and a shoulder 231a circumscribing the shaft of the pin is defined where the diameter changes. The shoulder 231a of the X-axis clevis pin 231 has a larger diameter than the opening in the cross-shaft member 250 through which the X-axis clevis pin 231 extends. Therefore, when the X-axis clevis pin 231 is threaded further toward its distal end by tightening the clevis pin 231, the shoulder 231a urges the cross-shaft member 250 against the X-axis hinge arm 241a (see FIGS. 4C and 4D). The inner surface 245 of the X-axis clevis arm 241a that contacts the cross-shaft member 250 and the corresponding contacting surface 255 of the cross-shaft member 250 are configured to frictionally or mechanically engage each other and lock the X-axis clevis 241 and the cross-shaft member 250 together. This locking prevents the X-axis clevis 241 from pivoting about the X axis relative to the cross-shaft member 250 and the Y-axis clevis 242. The inner surface 245 and the contacting surface 255 of the cross-shaft member 250 can be roughened surfaces, e.g., diamond teethed, knurled, etc. to generate the frictional or mechanical interference and aid in the locking. This locking configuration for the X-axis clevis 241 and the X-axis clevis pin 231 allows the X-axis clevis 241 to be locked at a variety of pivot angles with respect to the Y-axis clevis 242.

The Y axis can be locked by threading the threaded rod 214 into the Y-axis clevis 242 until the threaded rod 214 contacts the cross-shaft member 250 and tightening the threaded rod 214 against the cross-shaft member 250. By tightening the threaded rod 214 with sufficient force against the cross-shaft member 250, a sufficient frictional interference between the threaded rod 214 and the surface of the cross-shaft member 250 can be created to lock and prevent the Y-axis clevis 242 from pivoting about the Y axis. The cross-shaft member 250 has a substantially spherical shape whose center is located at the point of intersection of the pivot axis X and the pivot axis Y. The spherical shape allows the Y-axis clevis 242 to pivot about the pivot axis Y even with the threaded rod 214 extending through the clevis up to the cross-shaft member 250 but not quite in locking position.

To further enhance the frictional interference between the threaded rod 214 and the surface of the cross-shaft member 250, the respective contacting surfaces can be configured and adapted to increase the frictional force. For example, the outer surface of the cross-shaft member 250 can be provided with a desired surface roughness. The corresponding surface at the end of the threaded rod 214 that contacts the cross-shaft member 250 can also be configured appropriately to enhance the frictional interference between the two contacting surfaces. For example, the contacting surface of the threaded rod 214 also can be provided with a desired surface roughness. The contacting surface of the threaded rod 214 also can be provided with a concave contour matching the surface contour of the cross-shaft member 250 to increase the contact area between the threaded rod 214 and the cross-shaft member 250.

According to another embodiment, the cross-shaft member 250 is configured to enable locking of the Y-axis clevis 242 only at a single predefined angle with respect to the X axis. In the example shown in FIGS. 3A, 3C, 4A and 4C, a band of flat surface 252 is provided on the surface of the cross-shaft member 250 at least partially circumscribing the cross-shaft member 250 on the side facing the threaded rod 214 advancing through the Y-axis clevis. The band of flat surface 252 is oriented so that it extends parallel to the Y axis and orthogonal to the X axis. In other words, the band of flat surface 252 is positioned at the equatorial position on the cross-shaft member 250 if the X axis was viewed as going through the North and South poles of a globe represented by the spherical cross-shaft member 250. The equatorially positioned band of flat surface surface 252 allows the Y-axis clevis 242 to be locked only at a position orthogonal to the X-axis as shown. The threaded rod 214 threaded into the internally threaded hole 242h of the Y-axis clevis 242 would be oriented orthogonal to the X-axis. In an alternative embodiment, the band of flat surface 252 can be oriented at an angle that is not orthogonal with respect to the X axis in order to allow the Y-axis clevis 242 to lock only at that particular angle.

Referring to FIGS. 5-10B, the structure of the telescopically adjustable strut 100 will be described in more detail. The adjustable strut 100 has a generally elongated structure comprising two ends. Provided at each end is a universal joint connector 140A, 140B for connecting the adjustable strut 100 to orthopedic external fixator base members 21, 22. The adjustable strut 100 comprises an elongated shaft 102 with a hollow axial center 102c (shown in FIG. 7) and a lead screw 110, one end of which extends into the hollow axial center 102c.

Provided at one end of the elongated shaft 102 is the universal joint connector 140A. The universal joint connector 140A connects the elongated shaft 102 end of the adjustable strut 100 to a base member 21, 22 of the external fixator 20 while allowing the connection to be made at a variety of angles and directions. Provided at opposite ends of the strut 100 is a second universal joint connector 140B that is connected to the end of the lead screw 110. The universal joint connector 140B connects connects the lead screw 110 end of the adjustable strut 100 to another base member 21, 22 of the external fixator 20 while allowing that connection to be made at a variety of angles and directions. The term "universal joint connector" as used herein refers to a connector connecting two parts that is configured and adapted to bend or flex in a variety of angles.

The universal-joint connectors 140A, 140B can be any type of jointed or hinged connectors that provide robust articulation of the connection between the adjustable strut 100 and the base members 21, 22 of the external fixator 20. The robust articulation allows a variety of angular configurations for the two ends of the adjustable strut 100 attached to the base members 21, 22 of the external fixator 20.

Referring to FIGS. 7-9A, the structures of the universal-joint connectors 140A and 140B will be described in more detail. In the example of the strut 100 shown, the universal-joint connectors 140A, 140B have similar structure as the universal-joint hinges 240 shown in FIGS. 4A-4D. FIGS. 7 and 8 show the two pivot axes X and Y associated with the structure of the universal-joint connectors 140A, 140B. Similar to the universal-joint hinge 240, each of the universal-joint connectors 140A, 140B comprises two clevis connectors, an X-axis clevis 141 and a Y-axis clevis 142 that are pivotally connected by a cross-shaft member 150. The arrangement and interacting movement of the X-axis clevis 141 and the Y-axis clevis 142 is same as that of the corresponding devises in the universal-joint hinge 240. The X-axis clevis 141 connects the universal-joint connectors 140A, 140B to the shaft 102 or the lead screw 110. The Y-axis clevis 142 connects the universal-joint connectors 140A, 140B to the base members 21, 22 by Z-axis screws 160. The Z-axis screw 160 is inserted through one of the mounting holes 21h, 22h in the base members 21, 22 and threaded into the Y-axis clevis 142. An X-axis pin 131 and the Y-axis pin 132 correspond to the X-axis pin 231 and the Y-axis pin 232, respectively, of the universal-joint hinge 240.

Depending upon which end of the adjustable strut 100 is being considered, the X-axis clevis 141 is configured to be attached to either the shaft 102 or the lead screw 110 at its base portion. A variety of attachment methods and configurations can be used to attach the X-axis clevis 141 to the shaft 102 or the lead screw 110. In the illustrated example shown, the attachment between the X-axis clevis 141 and the shaft 102 and/or the lead screw 110 are enabled by a cross pin 180. This is better shown in detail in the longitudinal cross-sectional view of the adjustable strut 100 shown in FIG. 10A.

Referring to FIG. 9A, in one preferred embodiment, the X-axis clevis 141 and the cross-shaft member 150 are configured to enable locking of the X-axis to prevent the X-axis hinge 141 from pivoting about the pivot axis X. Except for the fact that the X-axis clevis pin 131 is not cannulated, the X-axis clevis pin 131 has the same structure as the X-axis clevis pin 231 of the universal joint hinge 240. The X-axis clevis 141 has a generally U-shaped structure and has two arms 141a, 141b with the cross-shaft member 150 positioned therebetween. The shaft of the X-axis clevis pin 131 extends from the first arm 141a, through the cross-shaft member 150, and to the second arm 141b through the openings provided in the arms 141a, 141b. The distal end of the X-axis clevis pin 131 threadably engages the arm 141a and is held in place. In order to prevent unintentional removal of the X-axis clevis pin 131, the distal end of the pin can be mechanically secured. In the example shown, a snap ring 135 is used to keep the X-axis clevis pin 131 from being removed. In another example, a cotter pin can be used in place of the snap ring 135.

According to a preferred embodiment, the universal joint connectors 140A, 140B are configured for locking the X and Y pivoting axes. This locking is accomplished in a similar manner to the universal joint hinge 240 by the operation of the X-axis clevis pin 131. The X-axis clevis pin 131 is configured to have a shoulder, like the shoulder 231a of the X-axis clevis pin 231, that urges the cross-shaft member 150 toward the X-axis clevis arm 141a (in the upward direction in FIG. 9A). The surfaces of the X-axis clevis arm 141a and the cross-shaft member 150 that contact each other are configured like the corresponding roughened contacting surfaces 245 and 255 of the universal joint hinge 240 to frictionally engage each other for locking the X-axis clevis 141 and the cross-shaft member 150 together.

The Y-axis clevis 142 can be configured to be locked for stopping the pivoting movement of the Y-axis clevis 142 about the pivot axis Y. The Z-axis screw 160 has an internally threaded longitudinal bore 167 and a Y-axis locking screw 170 is threaded into the longitudinal bore 167. As shown in FIG. 9A, the distal end 175 of the locking screw's stem extends out of the distal end of the Z-axis screw 160. As shown in FIG. 10A, as the locking screw 170 is threaded further into the Z-axis screw 160, the distal end 175 of the Y-axis locking screw 170 extends out of the Z-axis screw 160 until it contacts the cross-shaft member 150. Tightening the Y-axis locking screw 170 against the cross-shaft member 150 generates sufficient frictional interference between the distal end 175 of the Y-axis locking screw 170 and the cross-shaft member 150 and lock the Y-Y-axis hinge 142 in unison with the cross shaft member 150. This prevents any pivoting movement about the Y axis. As shown in FIGS. 9A and 10A, preferably, the terminal surface of the distal end 175 of the Y-axis locking screw 170 that contacts the cross-shaft member 150 has a concave contour so that the contacting surface area is a circle rather than a single point, thus, optimizing the frictional interference between the distal end 175 of the Y-axis locking screw 170 and the cross-shaft member 150.

As mentioned above, the base portion of the Y-axis clevis 142 is configured to be attached to a base member 21, 22 of the external fixator 20 by a Z-axis screw 160. The Z-axis screw 160 is threaded into the base portion of the Y-axis clevis 142 and has a cylindrical mid-section 165 that is smaller in diameter than the head portion 161 of the Z-axis screw 160. The mid-section 165 defines a gap between the head portion 161 of the Z-axis screw 160 and the Y-axis clevis 142 which accommodates the thickness of the base member 21, 22 of the external fixator 20. The Z-axis screw 160 is inserted through one of the mounting holes 21h, 22h in the base members 21, 22 and threaded into the base portion of the Y-axis clevis 142 to secure the strut 100 to the base member 21, 22. This is better illustrated in FIG. 1. The gap between the head portion 161 of the Z-axis screw 160 and the Y-axis clevis 142 is appropriately matched to the thickness of the base member 21, 22 such that when the strut 100 is attached to the base member 21, 22 and the Z-axis screw 160 is tightened, the base member 21, 22 gets locked between the Y-axis clevis 142 and the head portion 161 of the Z-axis screw 160 and the strut 100 is prevented from rotating about the Z-axis.

According to another embodiment, the universal-hinged connectors 140A, 140B can be implemented using other types of universally flexible joints other than the universal joint examples described above. FIGS. 11A-11B illustrate an example of an alternate type of connectors. FIGS. 11A-11B show a ball-joint 300 example. The ball-ball-joint 300 comprises a ball 302 that is captured between two ball-joint housing halves 312, 314. The first ball-joint housing half 312 threads onto the second ball-joint housing half 314. The internal structures of the two ball-joint housing halves 312, 314 are configured to form a spherical volume within which the ball 302 sits as shown in the cross-sectional view of FIG. 11B. The ball 302 has a stem 303 that extends out of an axially oriented opening in the first ball-joint housing half 312. The stem 303 has a terminal end 304 that is configured and adapted to receive and connect to either the lead screw 110 or the shaft 102 of the adjustable strut 100. In the example shown in FIGS. 11A, 11B, the terminal end 304 of the stem 303 is provided with an axially positioned hollow opening 305 for receiving either the lead screw 110 or the shaft 102. Similar to the adjustable strut example shown in FIGS. 1 and 5, a cross pin 180 can be utilized to keep the lead screw 110 or the shaft 102 attached to the terminal end 304 of the stem 303.

Threadably attached to the second ball-joint housing half 314 is a connecting piece 320 for attaching the ball-joint 300 to one of the base members 21, 22 of the external fixator 20. The connecting piece 320 has two threaded stem portions 322 and 324 extending in opposite directions. The first end 322 is threaded into the second ball-joint housing half 314 and the second end 324 is configured for attaching to one of the base members 21, 22. The connecting piece 320 has a middle portion 325 that is configured to accommodate turning by hand or a tool such as a wrench. In the illustrated example, the middle portion 325 has a six-sided nut like structure optimized for turning with an open-ended wrench. The second end 324 is threaded to receive a locking nut 330 for holding the base member 21, 22 between the middle portion 325 and the locking nut 330. When attaching the ball-joint 300 to one of the base members 21, 22, the second end 324 is inserted into one of the mounting holes 21h, 22h provided on the base members 21, 22 and held in place by threading the locking nut 330 on to the second end 324. The ball 302 swivels between the two ball-joint housing halves 312, 314 to allow adjustment of the attachment angle between the strut 100 and the base member 21, 22. Then the attachment angle can be fixed by locking the ball-joint 300. The locking is achieved by tightening the two ball-joint housing halves 312, 314 together and preventing the ball 302 from swiveling.

FIGS. 11C and 11D show another ball-joint 300a according to another embodiment for the universal-hinged connectors 140A, 140B. The ball-joint 300a comprises a ball 302 that is captured between two ball-joint housing halves 312 and 350. The first ball-joint housing half 312 threads onto the second ball-joint housing half 350. The internal structures of the two ball-joint housing halves 312, 350 are configured to form a spherical volume within which the ball 302 sits as shown in the cross-sectional view of FIG. 11C. The ball 302 has a structure similar to the ball 302 in the embodiment shown in FIG. 11B and is configured and adapted to receive and connect to either the lead screw 110 or the shaft 102 of the adjustable strut 100.

The second ball-joint housing half 350 is comprises a stem portion 352 for attaching the ball-joint 300a to one of the base members 21, 22 of the external fixator 20. The stem portions 352 has an externally threaded distal end 354 that extends through one of the mounting holes 21h, 22h provided on the base members 21, 22. The second ball-ball-joint housing half 350 is secured in place by a nut 330a that threads onto the distal end 354. In this embodiment, locking of the ball 302 is achieved by the use of a locking pin 340 that is received through the stem 352 of the second ball-joint housing half 350 from the distal end 354 of the stem 352. The stem 352 is cannulated and the locking pin 340 has a shaft 342 that is received through the cannulated stem 352. The shaft 342 of the locking pin 340 extends through the cannulated stem 352 and contacts the ball 302 by its distal end 345. The head of the locking pin 340 is provided with an annular recess 343 343 near the base of the shaft 342 for threadably engaging the externally threaded distal end 354 of the stem portion 352. The outer wall 344 of the annular recess 343 is threaded threaded for threadably engaging the threaded distal end 354 of the stem portion 352. By By threading the locking pin 340 to the second ball-joint housing half 350 and urging shaft 342 against the ball 302 until sufficient frictional interference is generated between the shaft 342 and the ball 302, the ball 302 can be prevented from swiveling and lock the ball joint 300a. The distal tip 345 of the shaft 342 can be configured to have a concave surface to optimize the surface area of the contact with the ball 302 and thus optimize the frictional interference generated. The nut 330a can be countersunk for accommodating the head of the locking pin 340 as shown in FIG. 11C to minimize the protrusion of the structures from the base members 21, 22.

Referring to FIGS. 7-10D, at the opposite end of the elongated shaft 102 is provided an adjustment knob 120 that is configured to threadably engage the lead screw 110 for telescopically adjusting the strut 100. The adjustment knob 120 is rotatably attached to the elongated shaft 102 to be axially rotated. The adjustment knob 120 can be rotatably attached to the end of the shaft 102 by an appropriate bearing mechanism 220. The bearing mechanism 220 can be secured to the adjustment knob 120 by an appropriate means known in the art. For example, the two pieces can be held together by press-fitting, welding, threading, a locking pin or adhesively attaching. The end of the shaft 102 can be provided with a flange 102a to keep the adjustment knob 120 assembly attached to the shaft 102. The adjustment knob 120 is provided with an axially-oriented opening 120c (shown in FIG. 7) through which the lead screw 110 extends into the hollow axial center 102c of the shaft 102.

The adjustment knob 120 is provided with a release button 122 that is movable between an engaged position and a released position. The release button 122 is configured to threadably engage the external threads of the lead screw 110 when in the engaged position and disengage from the external threads of the lead screw 110 when in the released position.

With the release button 122 in the engaged position, rotating the adjustment knob 120 relative to the lead screw 110 causes the lead screw 110 to linearly translate along the longitudinal axis of the shaft. Therefore, by the operation of the thread engagement between the release button 122 and the lead screw 110, the length of adjustment strut 100 can be adjusted to a desired length. Axially rotating the adjustment knob 120 in one direction retracts the lead screw 110 further into the shaft 102 and rotating the adjustment knob 120 in the opposite direction extends the lead screw 110 out of the shaft 102. FIGS. 5 and 6A show the strut 100 in fully retracted configuration and FIG. 6B shows the strut 100 in fully extended configuration.

In one preferred embodiment, the adjustment knob 120 is marked with directional markings 120m identifying the directions of rotation that will extend or retract the strut. For example, the adjustment knob 120 shown in FIG. 5 is marked with an arrow and a "+" character denoting that turning the adjustment knob 120 in the direction of the arrow will extend the strut 100.

Figure 6B:
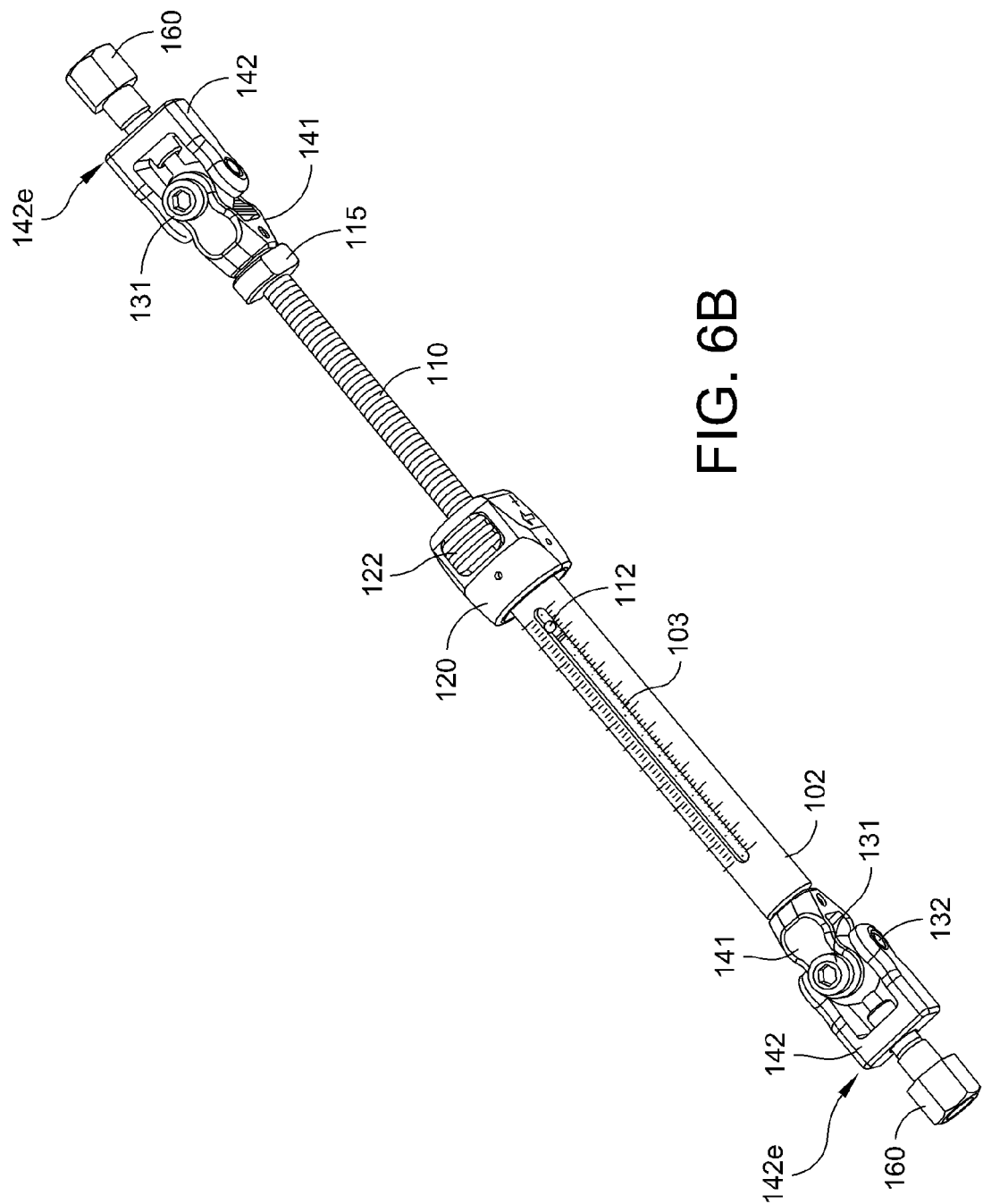
FIG. 6B is an isometric view of the adjustable strut of FIG. 5 in its extended configuration.

Referring to FIGS. 6A and 6B, in order to allow the adjustment knob 120 to rotate relative to the lead screw 110, the lead screw 110 and the shaft 102 are configured to prevent relative axial rotation of the lead screw 110 and the shaft 102. The shaft 102 is provided with a slot 103 extending along a side of the shaft 102 in the axial direction and a projection 112 provided on the lead screw 110 extends into the slot 103 so that the mechanical interference between the projection 112 and the slot 103 prevents axial rotation of the lead screw 110 relative to the shaft 102.

Threaded onto the lead screw 110 between the adjustment knob 120 and the universal joint connector 140B is a locking nut 115 for locking the adjustment knob 120 and preventing the adjustment knob 120 from turning. Thus, the locking nut 115 is used to fix the length of the strut 100 after being adjusted to a desired length. After the strut 100 is adjusted to a desired length by the use of the adjustment knob 120, the locking nut 115 is tightened against the adjustment knob 120 thus preventing the adjustment knob 120 from turning and locking the strut 100 at that particular length.

Figure 9C:
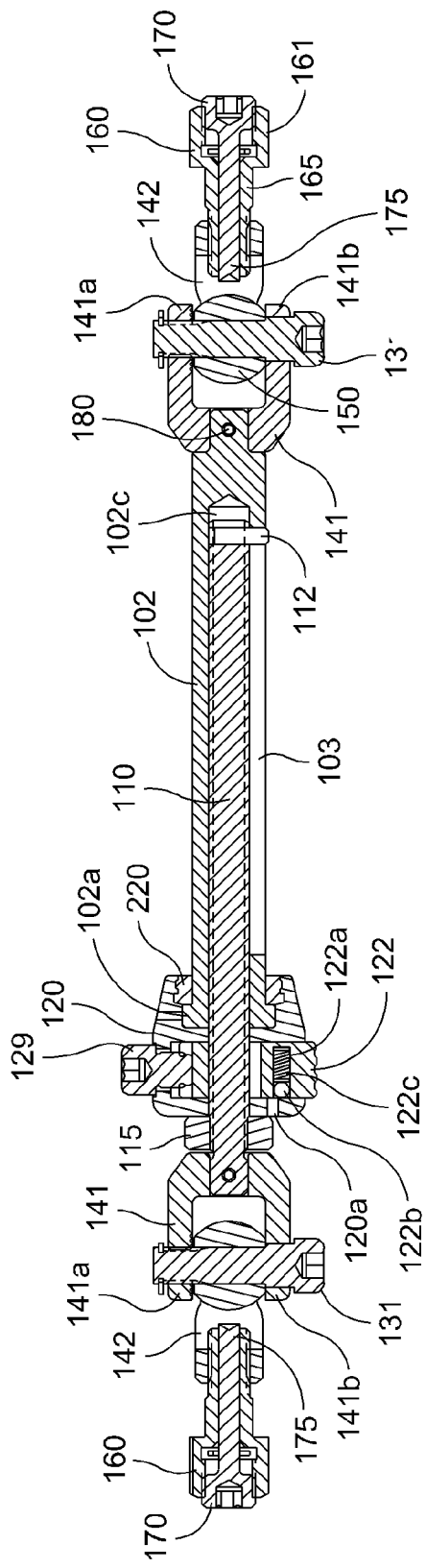
FIG. 9C is a longitudinal cross-sectional view of the adjustable strut shown in FIG. 9A with the adjustment knob in the engaged position.
Figure 9D:
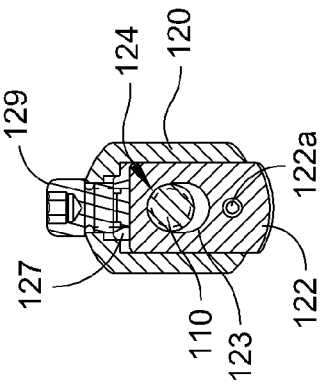
FIG. 9D is a transverse cross-sectional view through the adjustment knob shown in FIG. 9C in the engaged position.

FIGS. 9A and 9B show the release button 122 in the released position and FIGS. 9C and 9D show the release button 122 in the engaged position. The adjustment knob 120 has a recessed cavity 121 within which the release button 122 is situated. The cavity 121 is open at one end so that the release button 122 is exposed to allow a user to press it down into the cavity 121 when necessary. The release button 122 has an elongated opening 123 that is substantially in alignment with the axially-oriented opening 120c of the adjustment knob 120 so that the lead screw 110 extends therethrough. The elongated or oblong opening 123 is appropriately sized and has an internally threaded portion 124 on one side that engages the external threads of the lead screw 110 when the button 122 is in its engaged position.

In a preferred embodiment, the release button 122 is configured and adapted to be normally maintained in the released position shown in FIGS. 9A and 9B as the default position so that the length of the adjustable strut 100 can be quickly adjusted close or roughly to a desired length. The release button 122 can then be set to its engaged engaged position enabling fine adjustment of the strut's length by rotating the adjustment knob 120. For example, in the embodiment of the adjustment knob 120 shown in FIGS. 9A-9D, a ball detent mechanism 122b provided between the release button 122 and the adjustment knob 120 maintains the release button 122 in the released position shown in FIGS. 9A and 9B as the default position.

The ball detent 122b sits within a first recess 122a provided in the release button 122 and is urged outward by a coil spring 122c. A second recess 120a is provided in the side wall of the recessed cavity 121 that faces the ball detent 122b. The second recess 120a and the ball detent 122b are positioned so that the ball detent 122b and the second recess 120a comes into alignment when the release button 122 is in its released position. The ball detent 122b is partially urged into the second recess 120a by the coil spring 122c. The diameter of the second recess 120a is smaller than the diameter of the ball detent 122b so that the ball detent 122b only partially protrudes into the second recess rather than completely falling into the second recess 120a.

The release button 122 can be moved from the default released position shown in FIG. 9B to the engaged position shown in FIGS. 9C and 9D by threading the button-engaging screw 129 further into the adjustment knob 120. The advancing button-engaging screw 129 pushes the release button 122 until the internally threaded portion 124 of the oblong opening 123 engages the threads on the lead screw 110. A washer or a ring 127 attached to the distal end of the button-engaging screw 129 is provided for retaining the button-engaging screw 129 in place so that the screw 129 does not disengage from the adjustment knob 120 unintentionally.

Figure 10C:
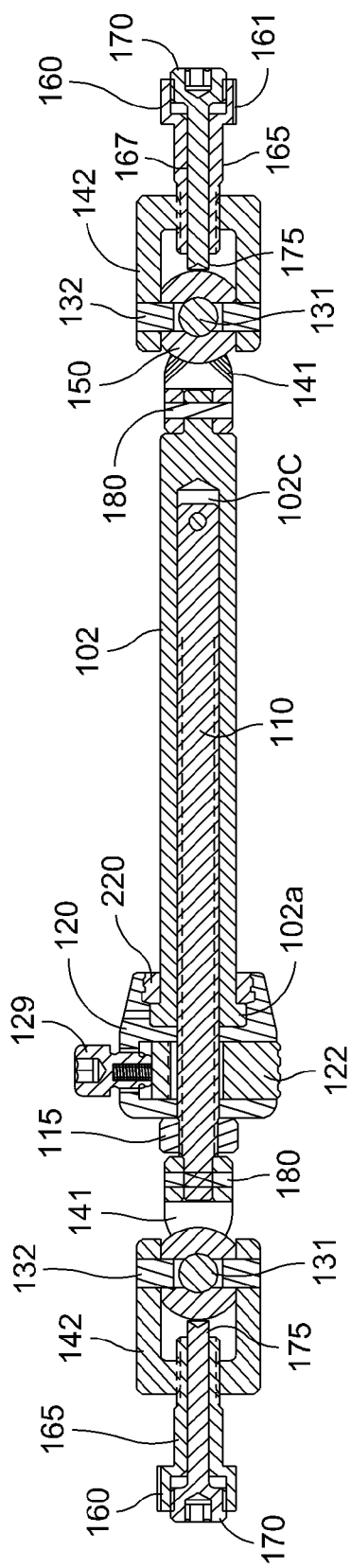
FIG. 10C is a longitudinal cross-sectional view of the adjustable strut shown in FIG. 10A with the adjustment knob in the released position.

FIGS. 10A-10D show the configuration of the release button 122 according to another embodiment. The release button 122 in this embodiment is configured to be normally in the engaged position. The release button 122 is spring-biased by an elastically compressible member 128 that is provided at the bottom of the cavity 121. The compressible member 128 can be a coil spring or a piece of an elastomeric material that can keep the release button 122 urged against the lead screw 110 as illustrated in FIGS. 10A and 10B.

Figure 10D:
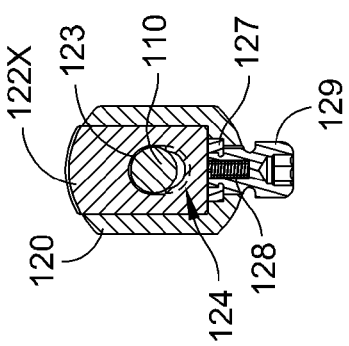
FIG. 10D is a transverse cross-sectional view through the adjustment knob shown in FIG. 10C in the released position.

Pressing the release button 122 in the direction of the arrow A shown in FIG. 10B disengages the release button 122 from the lead screw 110 and into the released position shown in FIGS. 10C and 10D. When the release button 122 is disengaged from the lead screw 110, the lead screw 110 is free to translate axially within the hollow axial center 102c of the shaft 102. Thus, the release button 122 can be used to quickly release the lead screw 110 and slide it in or out of the shaft 102 to adjust the length of the telescopically adjustable strut 100.

In addition to the spring-biasing member 128, a button-locking screw 129 also can be provided at the bottom of the cavity 121. The button-locking screw 129 is threaded into the adjustment knob 120 so that by threading the screw 129 further into the cavity 121 until the screw 129 contacts the release button 122, the release button 122 can be locked in its engaged position. Where the button-locking screw 129 is provided, an appropriate recess is provided in the button-locking screw 129 for holding the spring-biasing member 128 in place. A washer 127 can be places at the bottom of the cavity 121 to keep the button-locking screw 129 in the assembly.

In one embodiment of the present disclosure, the threads on the lead screw 110 and the release button 122 of the adjustment knob 120 are pitched such that a predetermined number of revolutions of the adjustment knob 120 about the axis of the shaft results in the lead screw 110 being axially translated by a desired incremental distance. For example, the threads can be pitched so that a known amount of revolution (e.g. one or more revolutions or a fraction of a revolution) of the adjustment knob 120 causes the lead screw 110 to axially translate a predetermined distance relative to the shaft 102. This facilitates measured, incremental extension of the adjustable strut 100 to accommodate the common practice of translating bone fragments a predetermined distance per day. The predetermined distance can be a fraction of a millimeter or more than a millimeter.

Referring to FIGS. 6A and 6B, the shaft 102 can further comprise graduated marks 105 provided along the slot 103, whereby the length of the strut is indicated by the location of the projection 112 relative to the graduated marks 115, the length of the adjustable strut 100 being defined by a predetermined end points on the strut. For example, the predetermined end points defining the length of the strut 100 can be the ends 142e of the two Y-axis clevis connectors 142 and the distance between the two ends 142e are indicated by the projection 112 and the graduated marks 105. Alternatively, the length of the strut can be defined as the distance between the two pivot axes X of the universal-hinged connectors 140A, 140B and the graduated marks 105 are marked accordingly to indicate that distance as indicated by the projection 112.

Thus, utilizing a plurality of the adjustable struts 100, two base members 21, 22 of an external fixator can be set to a particular configuration by adjusting the lengths of the adjustable struts 100 and the angles of attachment at either ends of the struts 100 via the universal-hinged connectors 140A, 140B.

The embodiments described in the foregoing disclosure are presented as examples. The scope of the present invention is to be limited only by the following claims.

What is claimed is:

1. An orthopedic fixation system, comprising:
   a universal joint including
      a ball from which a stem having a terminal end extends;
      a housing including a first portion and a second portion that together define a spherical internal volume that is sized and configured to receive the ball, the second portion including an elongate stem portion defining a hole that communicates with the spherical internal volume; and
      a locking pin including an elongate shaft and an outer wall that defines an annular recess, the elongate shaft of the locking pin being sized and configured to be received within the hole defined by the elongate stem of the second portion of the housing,
   wherein an internal portion of the outer wall of the locking pin includes threads for engaging threads disposed on a distal end of the elongate stem of the second portion of the housing, and
   wherein a distal end of the elongate shaft of the locking pin is configured to contact the ball to generate a frictional interference to lock the universal joint.

2. The orthopedic system of claim 1, wherein the terminal end of the stem defines a hollow opening sized and configured to receive one of a lead screw or a shaft.

3. The orthopedic system of claim 1, further comprising a locking nut for locking the universal joint to a base member.

4. The orthopedic system of claim 1, further comprising a telescopically adjustable strut including
   an elongated shaft defining a hollow axial center, and
   a lead screw having external threads, one end of the lead screw extending into the axial center of the shaft and the other end of the lead screw being coupled to the terminal end of the stem of the universal joint.

5. The orthopedic system of claim 4, further comprising a pair of ring-like base members and a locking nut, wherein the locking nut is configured to connect at least one of the ring-like base members to the second threaded stem portion of the universal joint.

6. The orthopedic system of claim 5, wherein the shaft defines a slot extending along a side of the shaft in the axial direction, and a projection is provided on the lead screw that extends into the slot, whereby the projection is visible through the slot and prevents axial rotation of the lead screw relative to the shaft.

7. The orthopedic system of claim 6, wherein the elongated shaft includes graduated marks provided along the slot, whereby the location of the projection relative to the graduated marks indicates the length of the strut, the length of the strut being defined by predetermined end points on the strut.

8. The orthopedic system of claim 7, further comprising an adjustable knob rotatably attached to one end of the elongated shaft, the adjustable knob defining an axially-oriented opening through which the lead screw extends and threadably engaging the external threads on the lead screw.

9. The orthopedic system of claim 8, wherein the external threads on the lead screw and the adjustment knob are pitched such that one or more complete revolution of the adjustment knob about the axis of the shaft causes the lead screw to axially translate a known incremental distance relative to the shaft.

10. An orthopedic fixation system, comprising:
    a universal joint including
       a first component including a ball and a stem;
       a second component and a third component that when coupled together define a spherical internal volume that is sized and configured to receive the ball therein, the third component including an elongate portion defining a hole that communicates with the spherical internal volume; and
       a fourth component including an elongate shaft and an outer wall that defines an annular recess, the elongate shaft being sized and configured to be received within the hole defined by the third component,
    wherein an internal portion of the outer wall of the fourth component includes threads for engaging threads disposed on a distal end of the elongate portion of the third component, and
    wherein a distal end of the fourth component is configured to contact the ball to generate a frictional interference to lock the universal joint.

11. The orthopedic fixation system of claim 10, wherein the outer wall of the fourth component is disposed at end of the elongate shaft of the fourth component.

12. The orthopedic fixation system of claim 10, further comprising a countersunk locking nut sized and configured to engage the outer wall of the fourth component.

13. The orthopedic fixation system of claim 10, further comprising a telescopically adjustable strut including
    an elonagated shaft defining a hollow axial center, and
    a lead screw having external threads, one end of the lead screw extending into the axial center of the shaft of the telescopically adjustable strut and the other end of the lead screw being coupled to an end of the stem of the first component of the universal joint.

14. An orthopedic fixation system, comprising:
    a universal joint including
       a housing defining a spherical internal volume that is sized and configured to receive a ball therein, a first component of the housing including an elongate portion that defines a hole that extends through the elongate portion and communicates with the spherical internal volume; and
       a locking pin including an elongate shaft and an outer wall disposed at one end of the elongate shaft, the elongate shaft being sized and configured to be received within the elongate portion of the first component of the housing to contact the ball,
    wherein an internal portion of the outer wall of the locking pin includes threads for engaging threads disposed on a distal end of the elongate portion of the of the first component of the housing.

15. The orthopedic fixation system of claim 14, wherein the housing includes a second component that is configured to engage the first component of the housing via a threaded connection.

16. The orthopedic fixation system of claim 14, further comprising a locking nut for locking the universal joint to a base member.

17. The orthopedic fixation system of claim 16, wherein the locking nut defines an opening that is sized and configured to slide along an outer surface of the elongate portion of the first component.

* * * * *